United States Patent [19]

Sugita et al.

[11] 4,360,023
[45] Nov. 23, 1982

[54] CEREBRAL ANEURYSM CLIP

[75] Inventors: Keiichiro Sugita, Nagoya; Gunji Nemoto, Matsudo, both of Japan

[73] Assignee: Mizuho Ika Kogyo Kabushiki Kaisha, Tokyo, Japan

[21] Appl. No.: 780,198

[22] Filed: Mar. 22, 1977

[30] Foreign Application Priority Data

Aug. 17, 1976 [JP] Japan ............... 51-110146[U]

[51] Int. Cl.³ ............................................. A61B 17/12
[52] U.S. Cl. ................................. 128/325; 128/346; 24/255 R
[58] Field of Search ............ 128/325, 346, 354, 321; 24/255 R, 137 R, 137 A; 29/243.56; 431/267, 273, 274, 275, 276; 126/25 B

[56] References Cited

U.S. PATENT DOCUMENTS

| 1,025,362 | 5/1912 | Beuoy | 128/321 |
|---|---|---|---|
| 1,741,457 | 12/1929 | Glass | 128/325 |
| 1,837,277 | 12/1931 | Lund | 128/321 |
| 2,583,020 | 1/1952 | Smith | 24/255 R X |
| 3,827,438 | 8/1974 | Kees | 128/325 X |

Primary Examiner—Michael H. Thaler
Attorney, Agent, or Firm—Ladas & Parry

[57] ABSTRACT

A metal wire guide member consisting of two leg portions and a straight guide portion connecting the two leg portions is secured to a cerebral anurysm clip with clamping jaws which are opened and closed by operating resilient arms supporting the jaws, in such a manner that the leg portions are fixedly embedded in the proximal portion of one of the jaws and in the supporting arm of the same jaw, respectively, and the straight guide portion is in pressing sliding contact with the other arm to guide the same along and press the same against the one arm whereby the jaws are correctly engaged with each other.

4 Claims, 9 Drawing Figures

CEREBRAL ANEURYSM CLIP

BACKGROUND OF THE INVENTION

This invention relates to an improvement of cerebral aneurysm clamps or clips.

Several types of cerebral aneurysm clips are known in the art. It is true that these conventional cerebral aneurysm clips have their own specific features. However, they do not satisfy all the conditions required for their use.

The cerebral aneurysm clip is a surgical instrument for clamping the base part of a cerebral aneurysm to permanently isolate the latter from the cerebral artery, and therefore it must be able to continuously maintain its clamping state with high reliability.

Since the operation for clipping a cerebral aneurysm is an extremely delicate one which is carried out at a deep, narrow part of the brain by optically magnifying affected part with a microscope, the cerebral aneurysm clip must satisfy the following conditions (1) through (5):

(1) The clamping pressure of the clip must be suitable for permanently isolating a cerebral aneurysm and for preventing the clip from being displaced or slipped off. As the clip can also be used for temporarily blocking the flow of blood in a normal blood vessel, the clamping pressure of the clip should not be so great as to give damage to a blood vessel, that is, it must be a certain pressure suitable for temporarily blocking the flow of blood.

(2) The opening degree of the clamping jaws of the clip must be greater than the size of a cerebral aneurysm, that is, it must be great enough to clamp the cerebral aneurysm.

(3) Since the clip is normally left permanently in the brain, the size of the clip must be as small as possible.

(4) In addition, the shape of the clip must be such that when clamping a cerebral aneurysm the operator can clearly see it without being blinded by the clip.

(5) The width of the jaws of the clip must be so small that the jaws can clamp a cerebral aneurysm across the narrow base part thereof.

In conventional cerebral aneurysm clips, it has sometimes experienced that they are displaced improperly from a desired clamping position and in the worst case they are slipped off the base part of a cerebral aneurysm to which they are applied. This is a serious problem because if the clip applied is slipped off it influences a human life.

SUMMARY OF THE INVENTION

Accordingly, an object of this invention is to provide a cerebral aneurysm clip which satisfies the above described conditions fully and is free from the above stated serious problem.

Another object of the invention is to provide a cerebral aneurysm clip having clamping jaws which never move out of correctly opposed clamping position once it is closed.

The manner in which the foregoing objects and other objects are achieved by this invention will become more apparent from the following detailed description and the appended claims when read in conjunction with the accompanying drawings.

DETAILED DESCRIPTION OF THE INVENTION

Figure 1:
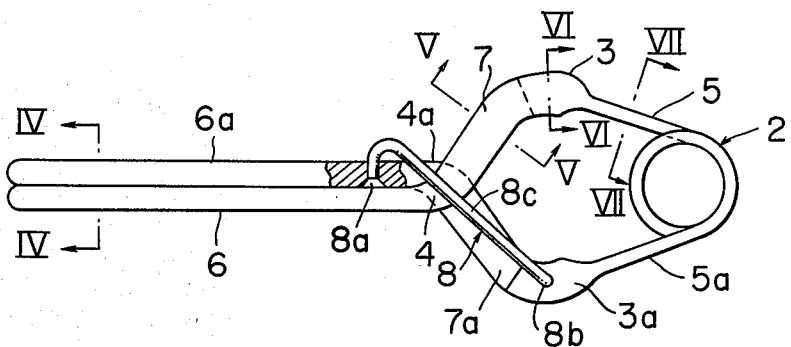
FIG. 1 is a plan view, with a part in section, illustrating a cerebral aneurysm clip according to this invention.
Figure 2:
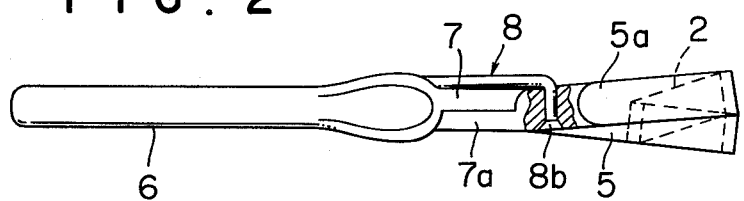
FIG. 2 is a side view, with a part in section, showing the cerebral aneurysm clip illustrated in FIG. 1.
Figure 3:
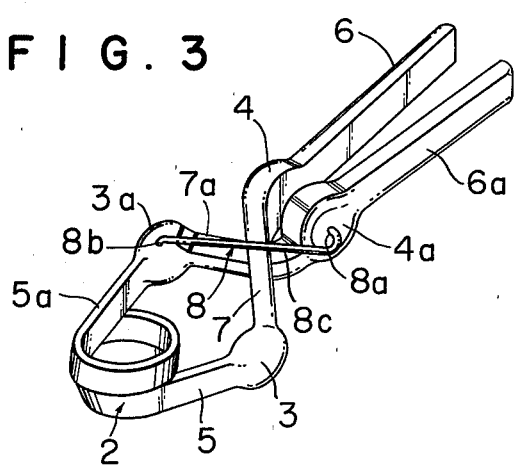
FIG. 3 is a perspective view of the clip shown in FIG. 1 and 2.
Figure 4:
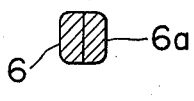
FIG. 4 is a cross section taken along the line IV—IV in FIG. 1.
Figure 6:
FIG. 6 is a cross section taken along the line VI—VI in FIG. 1.

The cerebral aneurysm clip according to the invention is formed by bending an elongated resilient material as shown in FIGS. 1, 2 and 3. More specifically, the elongated resilient material is wound in such a manner that a coil 2 is formed at its intermediate part and two substantially identical clipping or clamping arms are extended from the coil 2. The formation of the coil 2 is to give resiliency to the clip. It is to be noted that the length of each clamping arm is of the order of 20 mm. The two arms extended from the coil 2 are so bent inwardly at parts 3 and 3a of circular cross section shown in FIG. 6, equidistant from the coil 2 that the arms cross each other. The two arms are further twisted through 90 degrees at parts 4 and 4a equidistant from the parts 3 and 3a to form clipping or clamping jaws 6 and 6a which are kept in face-to-face abutting engagement with each other by the resiliency of the coil 2. It will be observed from FIG. 4 that the clamping jaws 6 and 6a have planar inner surfaces thereof in mutual abutting contact.

Figure 7:
FIG. 7 is a cross section taken along the line VII—VII in FIG. 1.

For convenience of description, the portions of the arms extending from the coil 2 to the parts 3 and 3a will be hereinafter referred to as "open arm sections 5 and 5a", and the portions of the arms extending between the parts 3 and 3a and the parts 4 and 4a as "cross arm sections 7 and 7a". The cross section of the sections 5 and 5a is as shown in FIG. 7.

Figure 5:
FIG. 5 is a cross section taken along the line V—V in FIG. 1.

It will be observed from FIGS. 3 and 5 that the mutually opposing sides of the cross arm sections 7 and 7a are formed flat to provide smooth face-to-face sliding contact between the cross arm sections. It will thus be understood that when the parts 3 and 3a and open arm sections 5 and 5a are forced or squeezed toward each other, the clamping jaws 6 and 6a will be moved apart and the clip will assume the open state shown in FIG. 3, and that when the force is removed the clip will assume the closed state shown in FIG. 1 with the jaws 6 and 6a in mutual abutment for clamping an object therebetween.

It is desirable that the cross-sectional shapes of the clip be made as shown in FIGS. 4 through 7 in order to provide optimum resiliency and clipping function.

In the operation of the clip, if the jaws 6 and 6a are brought in abutment in a state incorrectly opposed to each other or in a mutually offset state, the clamping force of the clip will be reduced when it has clamped an object, and as a result the clip may be displaced or in the worst case slipped off from the object.

In order to prevent such incorrect abutment of the jaws 6 and 6a which is caused by the fact that the cross arm sections 7 and 7a move apart from each other when the clip is to be closed, a guide member 8, preferably made of metal wire, is secured to the clip. More specifically, the guide member 8 comprises two relatively short leg portions 8a and 8b at the two ends thereof, and a relatively long straight guide portion 8c connecting the two leg portions, and the leg portions 8a and 8b are fixedly embedded in the proximal portion of the jaw 6a of one arm and in the part 3a of the same arm, respectively, in such a manner that the straight guide portion 8c of the guide member 8 extends in contact with that surface of the cross arm section 7 of the other arm, remote from the one arm and that the portion 8c lies in a plane parallel with the plane in which the opposing flat surfaces of the two cross arm sections 7 and 7a move in sliding contact with each other.

It will be understood that the guide member 8 is not obstructive to the sliding movement of the cross arm sections 7 and 7a and that it's straight guide portion 8c always presses the cross arm section 7 against the other cross arm sections 7a to keep the flat surfaces of these arm sections in tight contact. Since the straight guide portion 8c extends over the distance through which the cross arm section 7 slidingly moves along the other cross arm section 7a when the parts 3 and 3a and open arm sections 5 and 5a are squeezed toward each other, the pressing force by the guide member 8 is imparted over the entire operating range of the clip, whereby correct opposing abutment between the jaws 6 and 6a is always maintained and the clamping operation of the clip is kept in optimum condition.

Figure 8:
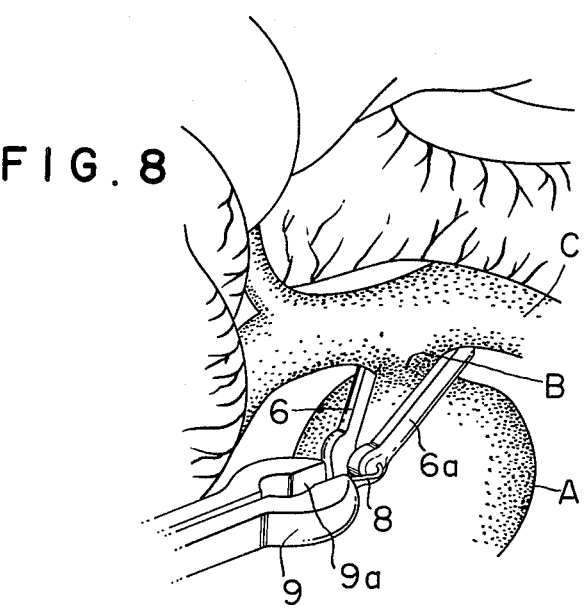
FIG. 8 is an explanatory view illustrating how the clip is used.

FIG. 8 illustrates how the clip shown in FIGS. 1 through 3 is used. In order to clamp the base part B of a cerebral aneurysm A, a clamping tool 9 is used. The clamping tool 9 has a clamping space 9a adapted to accommodate therein the open arm sections 5 and 5a and the parts 3 and 3a of the clip. The tool 9 has a construction similar to a pliers. After the open arm sections 5 and 5a, the parts 3 and 3a and the coil 2 are accommodated in the space 9a, the tool is manually operated to squeeze the open arm sections 5 and 5a toward each other. Then, the clip is opened and applied to the base part B of the aneurysm A. Thereafter, the manual squeezing force which has been applied to the tool is released and the clip is left on the part B. Thus, the cerebral aneurysm A is isolated from the cerebral artery C.

Figure 9:
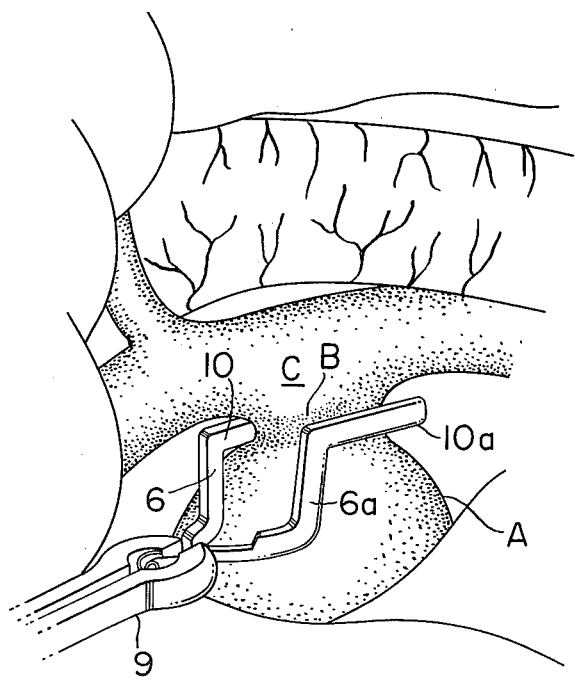
FIG. 9 is a view similar to FIG. 4 but showing a modified form of the clip.

FIG. 9 shows a modification of the clip. The only difference between the clip shown in FIGS. 1 through 4 and the modified clip is that in the latter the jaws 6 and 6a have bent free end portion 10 and 10a, respectively, so as to suit a particular application.

From the foregoing, it will be understood that the clip according to this invention is more reliable than conventional clips. It is to be noted that since the guide member is short and simple in construction, it does never obstruct the field of vision of the operator intending to apply the clip to the base part of a cerebral aneurysm. Accordingly the clip according to the invention is advantageous in that it can facilitate such a clamping operation as is performed for a narrow, deep diseased part in a brain.

What is claimed is:

1. A cerebral aneurysm clip comprising a coiled intermediate part and a pair of arms integrally extending therefrom, said arms including, respectively, open arm sections forming extensions of the coiled part, cross arm sections forming extensions of the open arm sections and which extend in mutually crossing and slidably engaging relationship, and have mutually opposed side surfaces which are formed flat to provide smooth face-to-face contact therebetween, and clamping jaws forming extensions of the cross arm sections and being urged in face-to-face abutting contact with each other by resiliency of the coiled part, and the clip further comprising a guide member made of metal wire and made up of an elongated straight guide portion and two relatively short leg portions, one of the leg portions being embedded in and fixedly secured to the jaw of one arm at a position adjacent to the cross arm section of said one arm, the other leg portion being embedded in and fixedly secured to said one arm at a position between the open arm section of said one arm and the cross arm section thereof, said straight guide portion lying in a plane spaced from and substantially parallel to the flat side surface of the cross arm section of said one arm, the cross arm section of said one arm and the straight guide portion of said guide member and being in sliding contact with said straight guide portion, whereby the straight guide portion applies force to the cross arm section of said other arm to urge it into contact with the cross arm section of said one arm, and wherein said one leg portion extends within said plane spaced from and substantially parallel to the flat side surface of the cross arm section of said one arm, whereas said other leg portion extends substantially perpendicular to said plane.

2. A cerebral aneurysm clip comprising a coiled intermediate part and a pair of arms integrally extending therefrom, said arms including, respectively, open arm sections forming extensions of the coiled part, cross arm sections forming extensions of the open arm sections and which extend in mutually crossing and slidably engaging relationship, and have mutually opposed side surfaces which are formed flat to provide smooth face-to-face contact therebetween, and clamping jaws forming extensions of the cross arm sections and being urged in face-to-face abutting contact with each other by resiliency of the coiled part, and the clip further comprising a guide member made of metal wire and made up of an elongated straight guide portion and two relatively short leg portions which are integrally formed with, and angularly bent from, the two ends respectively of the straight guide portion, one of the leg portions being embedded in and fixedly secured to the jaw of one arm at a position adjacent to the cross arm section of said one arm, the other leg portion being embedded in and fixedly secured to said one arm at a position between the open arm section of said one arm and the cross arm section thereof, and said straight guide portion lying in a plane spaced from and substantially parallel to the flat side surface of the cross arm section of said one arm, the cross arm section of the other arm of said pair lying between the cross arm section of said one arm and the straight guide portion of said guide member and being in sliding contact with said straight guide portion, whereby the straight guide portion applies force to the cross arm section of said other arm to urge it into contact with the cross arm section of said one arm.

3. A clip as claimed in claim 2, wherein each of said cross arm sections is substantially semi-circular in cross section.

4. A clip as claimed in claim 2, wherein each of said clamping jaws is of substantially uniform rectangular cross section.

* * * * *